US009359472B2

(12) United States Patent
Nicholson et al.

(10) Patent No.: US 9,359,472 B2
(45) Date of Patent: Jun. 7, 2016

(54) WATER-MEDIATED PREPARATIONS OF POLYMERIC MATERIALS

(71) Applicant: SECANT MEDICAL, INC., Perkasie, PA (US)

(72) Inventors: Charles Brendan Nicholson, Quakertown, PA (US); Jeremy J. Harris, Doylestown, PA (US); Peter D. Gabriele, Perkasie, PA (US)

(73) Assignee: The Secant Group, LLC, Telford, PA (US)

( * ) Notice: Subject to any disclaimer, the term of this patent is extended or adjusted under 35 U.S.C. 154(b) by 0 days.

(21) Appl. No.: 14/725,654

(22) Filed: May 29, 2015

(65) Prior Publication Data

US 2015/0344618 A1    Dec. 3, 2015

Related U.S. Application Data

(60) Provisional application No. 62/005,299, filed on May 30, 2014, provisional application No. 62/138,796, filed on Mar. 26, 2015.

(51) Int. Cl.
*C08G 63/12* (2006.01)
*C08G 63/20* (2006.01)
*C08G 81/00* (2006.01)
*C08G 63/81* (2006.01)
*C08G 63/78* (2006.01)
*A61K 47/34* (2006.01)

(52) U.S. Cl.
CPC ............... *C08G 63/12* (2013.01); *C08G 63/78* (2013.01); *C08G 63/81* (2013.01); *C08G 81/00* (2013.01); *A61K 47/34* (2013.01); *C08G 2230/00* (2013.01)

(58) Field of Classification Search
None
See application file for complete search history.

(56) References Cited

U.S. PATENT DOCUMENTS

| 4,632,964 | A  | 12/1986 | Altschuler et al. |
| 6,017,566 | A  | 1/2000  | Bunczek et al. |
| 6,444,782 | B1 | 9/2002  | Hamlin |
| 7,722,894 | B2 | 5/2010  | Wang et al. |
| 8,716,410 | B2 | 5/2014  | Venkatraman et al. |

(Continued)

FOREIGN PATENT DOCUMENTS

| EP | 0618249 A2 | 3/1994 |
| EP | 0618249 A3 | 3/1994 |

(Continued)

OTHER PUBLICATIONS

Jaafar et al. (Spectroscopic evaluation, thermal, and thermomechanical characterization of poly(glyercol-sebacate) with variations in curing temperatures and durations, J Mater Sci (2010) 45:2525-2529.*

(Continued)

*Primary Examiner* — Robert A Wax
*Assistant Examiner* — Melissa Mercier
(74) *Attorney, Agent, or Firm* — McNees Wallace & Nurick

(57) ABSTRACT

A process is provided for preparing a polymeric material through a water-mediated polymerization process that includes combining an alcohol monomer and an aqueous solution in a vessel, adding an acid monomer to the vessel, removing water from the vessel and producing the polymeric material from the vessel, wherein the polymeric material comprises a polyester of the alcohol monomer and the acid monomer. The methods described herein are particularly suitable for polymerization of poly(glycerol sebacate).

27 Claims, 6 Drawing Sheets

(56) References Cited

U.S. PATENT DOCUMENTS

2006/0009839 A1   1/2006   Tan
2009/0214373 A1   8/2009   Stinson et al.

FOREIGN PATENT DOCUMENTS

| WO | 00/55236 A1 | 9/2000 | |
| WO | 2009/009749 A1 | 1/2009 | |
| WO | WO 2009009749 A1 * | 1/2009 | ............... C09J 67/00 |
| WO | WO 2009067482 A1 * | 5/2009 | ............ A61F 2/0077 |
| WO | 2013/154780 A1 | 10/2013 | |

OTHER PUBLICATIONS

Barrere et al. (Polyester synthesis in aqueous miniemulsions, Polymer 44 (2003) 2833-2841).*

Sun et al. (The influence of lactic on the properties of Poly(glycerol-sebacate-lactic acid) 2009, pp. 178-182.*

Wang, Yadong et. al. A Tough Biodegradable Elastomer, Jun. 2002,vol. 20, Nature Publishing Group.

Gao, Jin et. al., Macroporous Elastomeric Scaffolds with Extensive Micropores for Soft Tissue Engineering, Wallace H. Coulter Department of Biomedical Engineering, Georgia Institute of Technology, Feb. 4, 2010, pp. 917-925, vol. 12, Mary Ann Lieber, Inc.

Jaafar, Israd et. al., Spectroscopic evaluation, thermal, and thermomechanical characterization of poly(glycerolsebacate) with variations in curing temperatures and durations, J. Mater Sci, Sep. 13, 2009, pp. 2525-2529, Springer Science+Business Media, LLC.

Pryor, Howard et al., Poly(glycerol sebacate) films prevent postoperative adhesions and allow laparoscopic placement,Surgery, pp. 490-497, vol. 146, No. 3, Boston, MA.

Guo, Xiao-Long et. al., Characterization and optimization of glycerol/sebacate ratio in poly(glycerol-sebacate elastomer for cell culture application, J. Biomed Mater Res Part A, Nov. 2014, pp. 3903-3907, vol. 102A, Issue 11, Society for Biomaterials.

Chen, Qi-Zhi et. al., Characterisation of a soft elastomer poly(glycerol sebacate) designed to match the mechanical properties of myocardial tissue, ScienceDirect, 2008, pp. 47-57, Biomaterials.

Sun,ZJ et. al., Materials Science and Engineering, The influence of lactic acid on the properties of Poly (glycerol-sebacate-lactic acid),2009, p. 178-182, C29.

* cited by examiner

WATER-MEDIATED PREPARATIONS OF POLYMERIC MATERIALS

CROSS-REFERENCE TO RELATED APPLICATIONS

This application claims the benefit of and priority to, U.S. Provisional Application No. 62/005,299, filed May 30, 2014 and to U.S. Provisional Application No. 62/138,796, filed Mar. 26, 2015, both are which are hereby incorporated by reference in their entirety.

FIELD OF THE INVENTION

The present invention relates generally to processes for preparing polymeric materials and more particularly, but not exclusively, to water-mediated processes for preparing biocompatible and/or bioabsorbable polymeric materials.

BACKGROUND OF THE INVENTION

Polymers are used extensively in the preparation of biomaterials. Certain biomaterials used in the field include biocompatible and/or bioabsorbable synthetic polymers that are composed of monomers having different affinities for water. For example, in certain polymers formed from glycerol and a diacid, the glycerol may be water soluble while the diacid is nearly insoluble. Thus, when biomaterials including these compounds are prepared, the process for such preparation may simply include adding the monomers neatly to a vessel and allowing them to react directly. Such processes may be problematic because the polymerization reaction may be difficult to control and modify. The products of such reactions may have inconsistent properties between batches, resulting in biomaterials that may fail to perform consistently.

One such method is described in U.S. Pat. No. 7,722,894, Wang et al. The '894 patent describes a process for creating poly(glycerol sebacate) via a polycondensation reaction that occurs under a specific identified reaction condition, namely an anhydrous polycondensation reaction carried out at 120° C. and a pressure of 1 Torr or less to yield a colorless elastomer. However, this method and the specific form of polymer that results have numerous drawbacks that restrict or prevent their satisfactory commercial use. Among the drawbacks are that the specific process conditions taught by the '894 patent do not actually yield an elastomer as described, but instead produce a high molecular weight resin. While further curing of this resin outside of the time periods described can in course still yield an elastomer, the conditions of initial polymerization result in a polymer with a high polydispersity that render it unsuitable for commercial production in certain applications, such as those requiring tight control over molecular weight distribution, including controlled release.

Due to these and other difficulties present in the field, there is an unmet need for processes of synthesizing polymeric materials, where such processes allow for control and modification of the polymerization reaction occurring therein. The present invention meets those needs.

BRIEF DESCRIPTION OF THE INVENTION

The present invention meets the needs in the field for tunable preparations of polymeric materials by providing water-mediated processes for preparing polymeric materials, including articles and bioabsorbable materials that may be prepared by such processes.

In a first aspect, the invention includes a method of preparing a polymeric material. The method includes combining an alcohol monomer and an aqueous solution in a vessel. Methods of the invention may provide for adding an acid monomer to the vessel, then refluxing the alcohol monomer, the aqueous solution, and the acid monomer in the vessel. The method includes removing water from the vessel, such as by distilling water from the vessel, as necessary. Additionally, the method includes producing the polymeric material in the vessel. In certain aspects of the invention, the polymeric material includes a polyester of the alcohol monomer and the acid monomer.

In another embodiment of the method of the invention, the alcohol monomer may include glycerol. Further, the aqueous solution may comprise a water-soluble agent. The acid monomer of the invention may include a diacid and, for example, the diacid may include a compound of the formula [HOOC$(CH_2)_n$COOH], where n=1-30. In a particular embodiment, the acid monomer may include malonic acid, succinic acid, glutaric acid, adipic acid, pimelic acid, suberic acid, azelaic acid, sebacic acid, or a combination thereof. Particularly, the diacid in the methods of the invention may be sebacic acid.

In other embodiments of the method of the invention, the steps of combining the alcohol monomer and the aqueous solution in the vessel, adding the acid monomer to the vessel, refluxing, distilling, and/or producing the polymeric material may include the steps of heating, stirring, and/or applying sub-atmospheric pressure as necessary to prepare the desired polymeric material.

In further embodiments of the method of the invention, the method may include adding a supplemental aqueous solution, an oligomer the polymeric material, and/or a co-monomer to the vessel.

In another aspect, the present invention includes an article of manufacture that may be prepared by the processes of the invention. And, in an additional aspect, the present invention includes a bioabsorbable polymeric material prepared by the water-mediated processes of the invention, wherein the polymeric material may include a filament, a fiber, a yarn, a braid, a knit material, a mesh, a sheet, a coating, a tube, or a combination thereof.

BRIEF DESCRIPTION OF THE DRAWINGS

The foregoing summary and the following detailed description of the exemplary embodiments of the present invention may be further understood when read in conjunction with the appended drawings, in which.

Wherever possible, the same reference numbers will be used throughout the drawings to represent the same parts.

DETAILED DESCRIPTION OF THE INVENTION

A significant need exists in the field of biomaterial preparation for processes that allow for easier material processing, better early stage reaction control, inclusion of temperature sensitive compounds and inclusion of water-soluble additives in the synthesis of polymeric materials composed of monomers, which have minimal affinities for water, such as, for example, poly(glycerol sebacate) (PGS).

Figure 1:
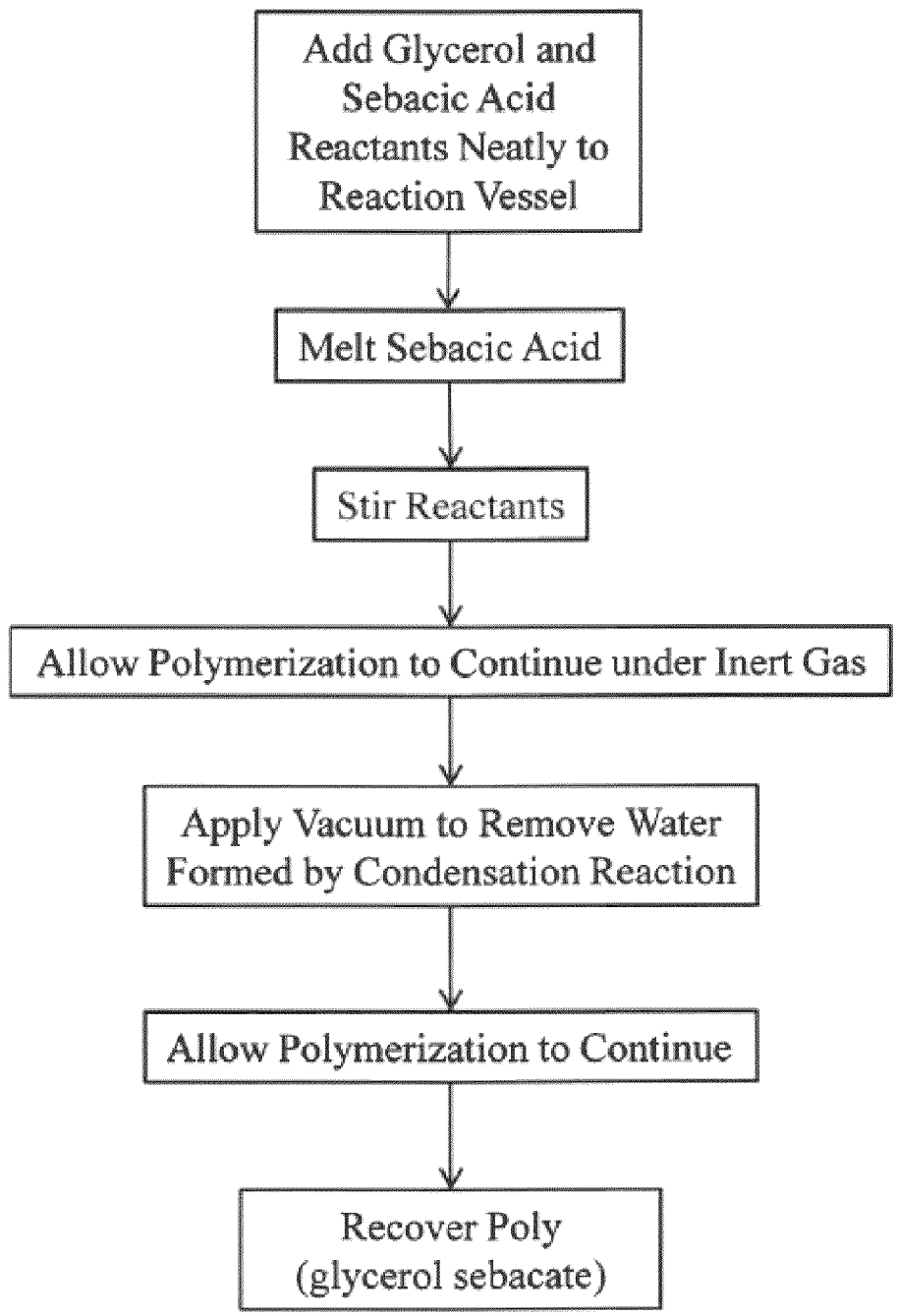
FIG. 1 schematically illustrates a known prior art method for preparing PGS where the polyol and diacid reactants are added together neatly in a vessel.

As demonstrated in FIG. 1, the polymer PGS may be synthesized by adding solid sebacic acid and liquid glycerol together and reacting them at about 120° C. for several hours. Sebacic acid has a melting point of 133-137° C. This means that the sebacic acid/glycerol mixture must initially be heated to temperatures greater than 133° C. to allow the sebacic acid to melt, and the two liquid reactants to be mixed. The melting of sebacic acid in the presence of glycerol is problematic because the reaction then takes place rapidly between the glycerol and the fraction of melted sebacic acid. Thus, the reaction conditions used in the art create difficulties in specifying the extent of the reaction as well as in controlling the reaction.

As set forth herein, the addition of water to the mixture before heating solves the melting problem by causing the sebacic acid to liquefy at a much lower temperature (between 100° C. and 105° C.). Additionally, because the reaction between a diacid (e.g., sebacic acid) and an alcohol or polyol (e.g., glycerol) is an ester condensation, and a product of this reaction is water, the reaction will not progress while a substantial amount of water is present in the reaction mixture. Indeed, the present disclosure may be contrasted to the prior art, which is replete with references that expressly recite anhydrous reaction conditions, such as the '894 patent discussed above.

As shown below with respect to the synthesis of poly (glycerol sebacate), water is a reaction product and thus the introduction of additional water into a system containing the reactants slows the reaction kinetics.

Figure 2:
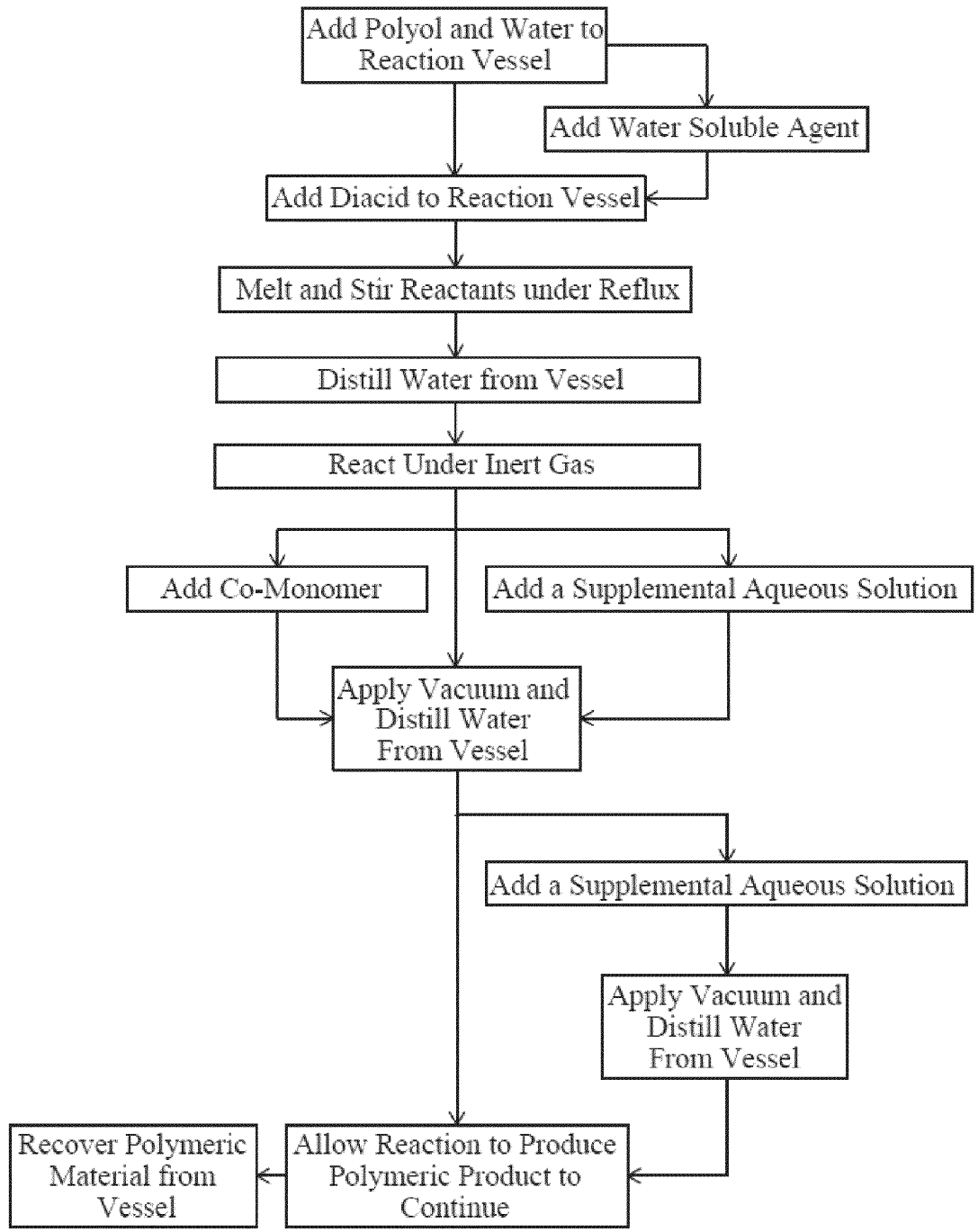
FIG. 2 illustrates a water-mediated method of preparing a polymeric material in accordance with an exemplary embodiment.

The problems in the field are solved by the present invention, which includes methods for preparing polymeric materials, such as the exemplary embodiment illustrated in FIG. 2. The polymeric materials, and biomaterials that may be prepared therefrom, may be biocompatible and/or bioabsorbable.

The methods of the invention that allow for the preparation of such polymeric materials may first include the step of combining an alcohol monomer and an aqueous liquid in a vessel. In certain aspects of the methods of the invention, a selected alcohol monomer, utilized in the polymerization of the polymeric material, and the aqueous solution may be combined or otherwise added together either sequentially or simultaneously into a vessel. As used herein, the term "polymer" or "polymeric" may include a homopolymer, copolymer, terpolymer, cross-linked polymer or the like. Moreover, the term "alcohol monomer," may refer to aliphatic alcohols having one or more hydroxy substituents and may, for example, include polyols having two or more hydroxy substituents. In certain aspects, the alcohol monomer may be glycerol.

As used herein the term "vessel" may refer to a beaker, bottle, canister, flask, bag, receptacle, tank, vat, jar, vial, tube, and the like that are generally known in the art to contain fluids or fluid-like materials and liquids.

The aqueous liquid of the invention may be water alone or be a solution of water and one or more water-soluble agents. The inclusion of water soluble agents allows for the incorporation of such agents into the polymeric material itself, where such agents would be difficult or impossible to provide without the aid of the present invention. Any thermally labile, water-soluble agents may be employed. Water-soluble agents in accordance with exemplary embodiments may include, for example, a vitamin, an anti-inflammatory agent, a protein, a protease, an herbicide, an aquarium food source, an anti-mitotic agent, an anti-platelet agent, an anti-coagulant agent, an anti-thrombotic agent, a thrombolytic agent, an enzyme, a chemotherapeutic agent, an antibiotic agent, an immunological adjuvant, a natural product, a scaffolding material, a processing agent, or a combination thereof. Vitamins of the invention may include water-soluble or non-soluble vitamins known in the art. Preferably, the vitamins of the invention

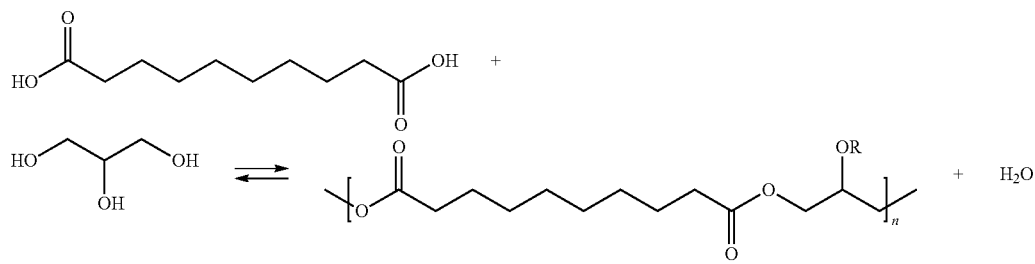

Once the added water is removed from the reaction, such as by distillation, the remaining reactants exist in liquid form, and are homogenously mixed, thus allowing the reaction to proceed in a controlled manner. Furthermore, because the amount of water added is known, a more reliable start time for the reaction can be calculated based on the measurement of the amount of water removed by distillation. That is, once the water initially added is removed, any additional water thereafter removed is water resulting as a product of the reaction.

may include vitamin B1, vitamin B2, vitamin B3, vitamin B5, vitamin B6, vitamin B7, vitamin B9, vitamin B12, vitamin C, or a combination thereof.

When water-soluble agents are incorporated or utilized in the process of the invention, they are provided in the polymeric material at a therapeutically effective amount and may be employed in pure form or, where such forms exist, in pharmaceutically acceptable salt, ester, or prodrug form. As used herein, the phrase "therapeutically effective amount" of the water-soluble agents of the invention means a sufficient amount of the agents as therapeutics in the treatment of a disorder, at a reasonable benefit/risk ratio applicable to any medical treatment.

The step of combining the alcohol monomer and the aqueous solution may take place at room temperature in the vessel or may include heating of the alcohol monomer and the aqueous solution to a temperature of about 50 to 200° C. In certain embodiments, the step of combining the alcohol monomer and the aqueous solution may include heating the alcohol monomer and the aqueous solution to a temperature of about 80 to 150° C. or, preferably, about 90 to about 110° C. Additionally, the alcohol monomer and the aqueous solution after combination may be heated for about 5 minutes to about 240 minutes, or about 30 minutes to about 180 minutes, or for a time sufficient to dissolve or homogenously disperse the alcohol monomer in the aqueous solution.

After the alcohol monomer and aqueous solution are combined in the vessel, an acid monomer may be added to the vessel and mixed with the alcohol monomer and aqueous solution. The acid monomer may be added neatly (i.e., without being dispersed or dissolved in solvent) to the vessel or may be added as a solution or mixture in a selected solvent. The acid monomer of the invention may include acidic compounds having one or more acid substituents including, but not limited to, monoacids, diacids, triacids, tetraacids, and the like. In certain aspects of the invention, the acid monomer is a diacid. Regarding diacids of the invention, such diacids may have the formula [HOOC(CH$_2$)$_n$COOH], wherein n=1-30. Preferably, the diacid of the invention may include malonic acid, succinic acid, glutaric acid, adipic acid, pimelic acid, suberic acid, azelaic acid, or sebacic acid. Particularly, the diacid of the invention is sebacic acid. In certain aspects, the alcohol monomer, acid monomer, and aqueous solution (e.g., water) may be provided in a molar ratio of about 0.5-5 mol alcohol monomer:0.5-5 mol acid monomer:0.5-5 mol water, with the alcohol monomer and acid monomer preferably present to achieve a molar equivalent of alcohol and diacid monomers. In a particular aspect, sebacic acid, glycerol, and water may be combined in molar ratio of about 1-2 mol sebacic acid, 1-2 mol glycerol, and 2-5 mol water.

Following addition of an acid monomer to the vessel, the contents of the vessel (e.g., alcohol monomer, aqueous solution, and acid monomer) may then be refluxed by heating the vessel. Refluxing the contents of the vessel provides, for example, melting of the acid monomer where the acid monomer is a solid. Indeed, an exemplary process may begin by adding water to the reaction mixture of glycerol and sebacic acid, thereby reducing the mixture's overall viscosity. This allows the mixture to be stirred easily. The water provides efficient heat transfer between reaction vessel walls and solid acid monomer (e.g., sebacic acid), allowing the acid monomer to melt quickly and form a dispersion. For example, sebacic acid is slightly soluble in water at room temperature, and this solubility is increased as the temperature increases. The suspension or colloidal mixture interaction further facilitates efficient liquefaction of the solid acid monomer. Moreover, the presence of the water in the mixture impedes the reaction of, for example, glycerol and sebacic acid, thus allowing all reactants to be molten and homogenous before the water is removed and the reaction substantially commences.

The step of refluxing the contents of the vessel may also include providing a condenser to the vessel in order to preserve the volume of solvent (e.g., water) contained within the vessel. Refluxing the contents of the vessel may include heating the contents to a temperature of about 50 to 200° C. or about 80 to 150° C. Preferably, the contents of the vessel are heated to a temperature of about 100 to 140° C. Additionally, the alcohol monomer, aqueous solution, and acid monomer may be heated for a selected period of time, which may include a period of about 1 to 336 hours or, more particularly, about 24 to 48 hours. Alternatively, where the acid monomer is a liquid or oil at room temperature, the step of refluxing may be avoided. It will further be appreciated that in some embodiments, the vessel may be pressurized to reach temperatures up to 200° C. or higher to shorten the time under reflux and/or for use in melting diacids that remain solid at high temperatures that could not otherwise be readily achieved.

After refluxing the contents of the vessel to achieve melting and thorough mixing of the reactants, the water added to the vessel to render that achievement is removed, such as through distillation or any process known in the art. The remaining reactants exist in liquid form, and are homogenously mixed, thus allowing the reaction to proceed in a controlled manner, which includes the production of additional water as a reaction by-product. That is, some of the water present in the vessel and subsequently removed is a result of its inclusion in the aqueous solution while some is present as the byproduct of the condensation reaction. By measuring the amount of water removed, it can be determined when the included water has all been removed, which gives a general idea of when the reaction shifts back toward the production of product, meaning that all reactants come to the reaction at the same time.

The step of distilling the water from the vessel may include heating the vessel to a temperature of about 50 to 200° C. or, particularly, about 80 to 150° C. In a particular aspect, the step of distilling the water from the vessel may include heating the vessel to a temperature of about 110 to 140° C., such as about 115° C., 120° C., 125° C., or 130° C. or any temperature or range of temperatures therebetween, although vacuum distillation at lower temperatures is also contemplated.

Following the distillation of the added water from the vessel, the alcohol and acid monomers can readily react and polymerize forming the polymeric material. Thus, the polymeric material is thereby produced directly from the vessel to yield the final product. Typically, producing the polymer material includes two separate steps after the added water is removed involving first heating under an inert gas followed by heating under application of vacuum, in which water of reaction is distilled from the vessel. Heating the contents of the vessel in these two steps (inert gas purge and vacuum) may be at the same or different temperatures from one another. The temperature may range from about 50° C. to about 200° C. or, particularly, about 80° C. to about 150° C. In a particular aspect of the invention, the contents of the vessel may be heated to a temperature of about 100° C. to 140° C., such as about 115° C. to about 135° C., such as about 115° C., 120° C., 125° C., 130° C. or 135° C. or any temperature or range of temperatures therebetween.

Regarding the heating of the vessel and/or the contents of the vessel in any of the process steps described herein, the heating of the vessel and/or its contents may be performed by conductive heating, convective heating, radiative heating, or a combination thereof. With respect to radiative heating, the vessel and/or its contents may be heated with, for example, microwave radiation and/or infrared radiation.

The distillation may occur in conjunction with stirring and/or purging the contents of the vessel by reaction under an inert gas, such as following an initial distillation step after reflux to remove the water added as a processing aide. As used herein, the term "inert gas" may refer to nitrogen, carbon dioxide, a noble gas, or a combination thereof. For example, noble gases of the invention may include helium, neon, argon, and the like. In certain aspects, the inert gas is nitrogen. The process of the invention may include purging the contents of the vessel with an inert gas at a rate of about 1 mL/min to about 10 L/min, such as while heating in the range of temperatures previously described. Moreover, inert gas purging of the vessel may be provided for a period of about 1 minute to about 48 hours or, more particularly, for about 1 hour to about 24 hours and preferably is conducted at atmospheric pressure, although carrying out this step at higher or lower pressures is contemplated.

Distillation may include heating and/or applying sub-atmospheric pressure to the vessel, and in particular distillation to remove water of reaction following the inert gas purge step of producing takes place through the application of a vacuum. For instance, distilling may include connecting a source of sub-atmospheric pressure to the vessel according to any process known in the art (e.g., a fluidic connection of a peristaltic pump, diaphragm pump, rotary pump, etc.). Sub-atmospheric pressure may be applied to the vessel at a pressure of less than about 760 Torr or, particularly, at a pressure of about 40 mTorr to 50 Torr. In another aspect, sub-atmospheric pressure may be applied to the vessel at a pressure of about 5 to 20 Torr, such as about 10 Torr.

Additionally, the sub-atmospheric pressure may be applied to the vessel at a constant pressure for a selected period of time or the sub-atmospheric pressure may be varied during the course of its application. For example, the application of subatmospheric pressure may include a stepwise reduction from a first pressure to a second pressure, such as a first pressure less than about 760 Torr and the second pressure greater than about 40 mTorr, particularly, greater than 1 Torr.

The distillation of water from the vessel may include heating and/or applying sub-atmospheric pressure to the vessel for a selected period of time. For example, the heating and/or application of sub-atmospheric pressure to the vessel may be applied for about 1 hour to 336 hours or, more particularly, about 12 hours to 168 hours. In a particular aspect, the heating and/or application of sub-atmospheric pressure to the vessel may be applied such as about 24, about 25 hours, about 26 hours, about 27 hours, up to about 48 hours, or any time or range of times therebetween.

In another aspect, the reactants (e.g., the alcohol and acid monomers) may be allowed to react under the application of sub-atmospheric pressure in addition to, or instead of, heating the reactants. Indeed, sub-atmospheric pressure may be applied to the vessel at a pressure of less than about 760 Torr or, particularly, at a pressure of about 40 mTorr to 50 Torr. In another aspect, sub-atmospheric pressure may be applied to the vessel at a pressure of about 1 to 50 Torr, such as 5 to 20 Torr, such as about 10 Torr. The polymerization of the alcohol and acid monomers may continue (with or without heating and/or applying sub-atmospheric pressure) for about 1 hour to 336 hours or, particularly, about 12 hours to 168 hours. In a particular aspect, the polymerization (i.e., production of the polymeric material) may continue for about 24 to 120 hours, including about 24 hours, about 25 hours, about 26 hours, about 27 hours, up to about 48 hours, up to about 76 hours, or any time or range of times therebetween.

Upon completion of the polymerization reaction to produce the polymeric material, the resulting polymeric material, which may be in the form of a moldable, pliable resin, is removed from the vessel and stored as necessary or required. Additionally, completion or progress of the processes of the invention may be determined by any means known in the art including, but not limited to, FTIR, DCS, SEC, TGA, LCMS, and/or NMR. Among the advantages are that the resulting product is resin that can be subsequently processed and then cured into any size, shape to any level of cross-linking as may be desired for a particular application or can be used in the resin form without any appreciable cross-linking for use, for example, as a coating.

In another aspect, a supplemental aqueous solution may optionally be provided to the vessel during the course of the process. For example, the supplemental aqueous solution may be added during the refluxing step, initial distillation step, and/or producing step while the reactants are left to polymerize into the polymeric material. The supplemental aqueous solution may include additional agents that may be incorporated into the resulting polymeric material. For example, agents that may be heat sensitive may be provided at a later stage in the reaction after some polymerization has taken place. The supplemental aqueous solution of the invention may include a vitamin, an anti-inflammatory agent, a protein, a protease, an herbicide, an aquarium food source, a growth factor, a glycoprotein, a proteoglycan, an anti-mitotic agent, an anti-platelet agent, an anticoagulant agent, an anti-thrombotic agent, a thrombolytic agent, an enzyme, a chemotherapeutic agent, an antibiotic agent, an immunological adjuvant, a natural product, a scaffolding material, a processing agent, or a combination thereof. As used herein, the term "scaffolding agents" may include, but is not limited to hydroxyapatite, chitosan, collagen, an alginate, polysaccharide, glycosaminoglycan, or a combination thereof. Moreover, as used herein, a "processing agent" of the invention may include, but is not limited to an agent for preparing a putty, an agent for preparing a dispersion, a surfactant, a dye, a pigment, a bio-active material, a non-bio-active material (e.g., a non-bio-active mesh coating), a brightening agent, or a combination thereof.

Without being confined to any one theory of the invention, it is believed that in the early stages of the reaction, oligomeric fractions are formed, and in later stages of the reaction, these oligomeric fractions are polymerized together. In the example of sebacic acid, the acid melts between 133° C. and 137° C., but the oligomeric fractions melt at much lower temperatures (about 45° C.). For example, once molten and mixed with glycerol, the sebacic acid/glycerol mixture may stay molten above 115° C. Thus, elevated temperatures may be necessary for the beginning of the reaction, but when oligomeric fractions are formed, the reaction continues at much lower temperatures. In certain aspects of the invention, oligomers of PGS (OGS) may be prepared by either methods of the present invention or other methods known in the art, and may be added during the method of the invention. Thus, it will be appreciated that in some embodiments, the process may be stopped at a time such that the polymeric material formed is still in the form of oligomeric fractions.

Indeed, an extension of these findings indicates that the oligomeric fractions may be synthesized, then brought to lower temperatures (e.g., about 60° C.). To these oligomers, an aqueous solution or supplemental aqueous solution that includes additional agents for incorporation into the polymeric material that may be thermally unstable above this temperature can be added while mixing. Sub-atmospheric pressure can then be applied to remove the added water provided by the aqueous solution after the additive is homogenously dispersed, and the reaction can continue to completion at the lower temperature.

Furthermore, additional monomers or even polymers may be utilized in the invention and added to the vessel during at least one of the refluxing, distilling, and producing steps to form polymeric materials composed of three or more monomers. Additional co-monomers may include a diacid, as defined above, or may include other monomeric units known in the art such as lactic acid, glycolic acid, caprolactone, hexamethylene diisocyanate, methylene diphenyl diisocyanate, and the like. In alternative aspects of the invention, PGS or other polymers formed in accordance with exemplary embodiments described herein may be subsequently reacted with other polymers such as poly(lactic acid), by way of example only. These polymers may be added at any stage during or after completion of the initial polymerization reaction, such as after the inert gas step but before vacuum, during vacuum, or even after the initial polymeric material has been formed and removed from the vessel in a separate reaction.

In some embodiments employing PGS, the co-polymers demonstrate an increase in the elasticity over neat PGS, while also decreasing the tensile modulus and tackiness of the material. A PGS/PLA copolymer does not require a secondary treatment to become elastomeric and also has a lower surface energy than neat PGS, resulting in the ability to coat hydrophobic substrates such as silicone, PTFE and polypropylene.

Another advantage of the copolymer compositions is the additional control afforded to the degradation kinetics and subsequent release kinetics of the composition. PGS is a surface eroding polymer while PLA is a bulk eroding polymer. Both mechanisms result in varied degradation kinetics which ultimately control the mechanical properties and release kinetics over the degradation time of the material. Depending on the end use of the material the co-polymer composition can be tailored to provide the appropriate degradation profile.

Any desired ratio may be employed; in one embodiment, a copolymer having a molar ratio of 90% PGS to 10% PLA or other co-polymer/co-monomer is provided. In another embodiment, the ratio is 50/50. Any other desired ratio may also be employed, such as any ratio in which the co-polymer/co-monomer content is less than 90:10, greater than 10:90, such as greater than 50:50, or any points in between.

Moreover, monofunctional or polyfunctional compounds may be added to the vessel during the method of the invention. For example, monofunctional or polyfunctional compounds may be added during at least one of the refluxing, distilling, and producing steps to enable modification of the surface energy properties of the polymeric material produced by the methods of the invention. A "monofunctional compound" of the invention may include, for example, an organic compound having one functionality, which may be a carboxyl, ester, amide, hydroxyl, epoxide, carbonate, amine, ester, carbamate, urea, carbonyl, sulphonamide, and the like. A "polyfunctional compound" of the invention may include, for example, an organic compound having two or more functionalities selected from the group consisting of carboxyl, ester, amide, hydroxyl, epoxide, carbonate, amine, ester, carbamate, urea, carbonyl, sulphonamide, or combinations thereof. Depending on the number and type of such compounds used in the methods described herein, surface energy properties of the resulting polymeric material may be modified in a controlled manner.

The process of the invention may include stirring the contents of the vessel at a rate of about 1-1000 RPM or, more particularly, at a rate of about 100-500 RPM. Indeed, the process of the invention includes mixing the acid and alcohol monomers (e.g., sebacic acid and glycerol) by stirring the mixture under high shear to facilitate the mixing of solid acid monomers and liquid alcohol monomers. Additionally, by adding water to the reaction mixture, the amount of shear necessary to stir is greatly reduced. For example, stirring the reactants is possible prior to melting the sebacic acid, for example, if water is present, but is impossible until the sebacic acid is molten in the absence of water. Earlier stirring is preferable because it allows for more thorough mixing of the reactants, which allows for a more consistent product.

An additional advantage of stirring reactants in combination with water mediation is that the vessel contents are essentially isothermal, resulting in better thermal management compared to a standard polymerization process in which heat at the walls is greater than at the center of the reactor while at elevated temperature as the sebacic acid starts to melt, exacerbating the problems with the standard process as the reaction proceeds to form large molecular weight polymers at the tank walls while the reactants at the center form smaller molecular weight fractions.

Water mediation has also been observed to impact particle size in the polymer resin which in turn may affect the resin's blending/copolymerization characteristics, solubility, and coating characteristics, or a combination thereof, among others. In particular, water mediated methods in accordance with exemplary embodiments evidence smaller particle size and a narrower distribution over conventional methods of synthesis. Particle size may impact the degradation rate, cross-link density, drug-loading capacity, mechanical properties or a combination thereof in any thermoset elastomer formed from the resin. For example, among the advantages are that a narrower distribution means that degradation time of the elastomer within the body can be better approximated. As a result, the thermoset elastomer can more reliably be used for controlled release of active ingredients incorporated during initial formation.

In some embodiments, PGS homopolymeric material formed in accordance with exemplary embodiments of the invention have a weight average molecular weight of less than 20,000 g/mol, such as less than about 15,000 g/mol. Some exemplary embodiments have a polydispersity index of less than 7.5, such as less than about 7 and in some embodiments, about 6.5 or lower. In other embodiments, such as PGS/PLA copolymers, for example, the weight average molecular weight achieved through exemplary embodiments may be up to 130,000 g/mol or higher.

According to the process of the invention, a bioabsorbable or biocompatible polymeric material may be manufactured. The bioabsorbable polymeric material may further comprise a filament, a fiber, a yarn, a braid, a knit material, a mesh, a sheet, a coating, a tube, or a combination thereof. In a particular aspect, the polymeric material includes poly(glycerol sebacate) that may or may not incorporate a vitamin, an anti-inflammatory agent, a protein, a protease, an herbicide, an aquarium food source, a growth factor, a glycoprotein, a proteoglycan, an antimitotic agent, an anti-platelet agent, an anti-coagulant agent, an anti-thrombotic agent, a thrombolytic agent, an enzyme, a chemotherapeutic agent, an antibiotic agent, an immunological adjuvant, a natural product, a scaffolding material, a processing agent, or a combination thereof.

In another embodiment of the invention, the processes disclosed herein may be used to prepare emulsions of the polymeric material for 3D printing. For example, an emulsion of PGS may serve as a bio-ink that may be printed onto a substrate using a 3D printer. For example, the polymeric materials of the invention may include scaffolding materials (e.g., hydroxyapatite) to allow for the preparation of a bio-ink that may be printed to bone using a 3D printer as known in the art.

The foregoing processes provide specific advantages over the prior art. For example, it is advantageous to be able to introduce water soluble additives to the reaction mixtures at different stages because it allows for options in doping the polymeric materials produced by the present process. For example, PGS is a water immiscible polymer, so water soluble additives such as common active pharmaceutical ingredients, therapeutic biological agents, and processing aids would be very difficult to effectively and homogenously disperse throughout the reactant mixture. However, by providing the present process that includes the use of water or aqueous solutions, the water soluble molecules that can be added may be homogenously mixed into the reactant matrix, forming a dispersion once the water is removed.

The present invention provides distinct advantages in the field by allowing for the controlled preparation of polymeric materials that may be prepared with consistency between batches. Moreover, by utilizing water as a medium prior to the commencement of the reaction, the polymerization between alcohol and diacid may be initiated at lower temperatures as compared to the reaction between alcohol and diacid being performed neat in the absence of an aqueous solvent. Utilizing these methods in the presence of an aqueous medium rather than a non-aqueous or organic solvent system also provides other distinct advantages. For example, the use of organic solvents generally reduces the boiling point of the process and may hinder the miscibility of certain reactants, such as limitations on water soluble active ingredients. Residual organic solvents may also have safety and regulatory concerns, whereas water does not share the same health or safety issues. Additionally, when scaling up such polymerization reactions that might ordinarily be performed neat, the present process allows for a drop in mixture viscosity due to the presence of water where, ordinarily, the viscosity of a neat polymerization would render the reaction difficult or nearly impossible to stir.

The addition of water to the reaction mixture may stall the reaction until the water is removed to allow for homogenous mixing of the reactants. Regarding PGS specifically, PGS may be degraded to its reactant species by the addition of water. Any PGS that may have been synthesized would ordinarily be degraded. Accordingly, in most preparations involving PGS, water is expressly eliminated from all parts of the reaction. An inert gas, such as nitrogen gas, may be used to purge the reaction system, with the application of sub-atmospheric pressure, to remove trace water produced by the condensation from the reaction. However, the approach described herein demonstrates that water may be used as a processing aid in the preparation of polymeric materials, such as the polyester PGS, without degradation.

Exemplary embodiments are also directed to biocompatible, bioresorbable, bioabsorbable, and/or biodegradable polymers formed according to one or more of the methods disclosed herein that include a uniform or substantially uniform morphology, molecular weight distribution, molecular weight fraction, monomer distribution, and/or degree of polymerization. For example, in one embodiment, the water mediated synthesis reduces or eliminates reaction of the acid and alcohol monomers until after distillation, which increases a uniformity of reaction throughout the vessel as compared to non-water mediated methods. In another embodiment, the increased uniformity of reaction reduces or eliminates different reaction rates and/or lengths throughout the vessel, forming the polymer having increased uniformity as compared to polymers formed through non-water mediated methods.

The uniformity of the polymer formed through water mediated synthesis facilitates a controlled release of active agents from the polymer, such as antimicrobial agents. In one embodiment, the controlled release is adjusted through manipulation of the polymerization conditions of the method. For example, adjusting the reaction temperature, pressure, and/or duration during one or more steps in the method modifies the finished polymer/oligomer structure, providing control of the release kinetics. The modifications to the finished structure include, but are not limited to, modifications in morphology, molecular weight fractions, molecular weight distribution, fraction composition, and/or a degree of polymerization of the finished product. These modifications may vary the release kinetics of the antimicrobial article formed therefrom by, for example, modifying the release rate, modifying a size of the fractions released during degradation, modifying a porosity of the antimicrobial article, modifying a fraction composition of the antimicrobial article, or a combination thereof.

The antimicrobial agents include any component or compound having antimicrobial properties. Suitable antimicrobial agents include, but are not limited to, additives dispersed in the polymer, additives incorporated into the polymer as well as monomers of the polymer and portions of the polymer released during degradation, or some combinations thereof. For example, one antimicrobial article includes poly(glycerol sebacate) (PGS) itself, the monomers and/or oligomers of which provide antimicrobial properties upon release. Another antimicrobial article includes a non-toxic antimicrobial agent derived from human metabolites and provided in biodegradable polymeric form. Without wishing to be bound by theory, it is believed that the sebacic acid and/or glycerol monomers of PGS provide the antimicrobial properties through quorum quenching or quorum sensing inhibition (QSI). The QSI of the PGS monomers disrupts the quorum sensing of microbial organisms, such as bacteria, resulting in the microbial organisms remaining in a non-virulent state and/or preventing differentiation into a pathogenic colony. Although described herein primarily with regard to water mediated synthesis, as will be understood by those skilled in the art, the antimicrobial properties of the polymers, such as PGS, are not dependent upon any specific formation process. Rather, the PGS and its repeating units and/or monomers will retain the antimicrobial properties disclosed herein.

Additionally or alternatively, the polymer formed according to one or more of the methods disclosed herein includes additives that provide and/or increase the QSI of the antimicrobial article. Suitable additives include, but are not limited to, reactable Tween® products (commercially available from Sigma-Aldrich®); quorum sensing molecules and/or analogs of quorum sensing molecules such as, but not limited to, cis-2-decenoic acid, cis-2-dodecenoic acid, cis-11-methyl-dodecenoic acid, 12 methyl-tetradecanoic acid, cis-9-ocatdecanoic acid, tetradecanoic acid, linoleic acid, oleic acid, palmitic acid, stearic acid, lauric acid, myristic acid, sapienic acid, cis-8-octadecenoic acid, cis-11-methyl-2-dodecenoic acid, 4,5-dihydroxy-2,3-dipentadione, cyclic adenosine monophosphates, alarmones (ppGpp and pppGpp), cyclic di-GMP, N-acyl homoserine lactones, diketopiperazines, 4-quinlones (2-heptyl-3-hydroxy-4-quinlone and 2-heptyl-4 (1H)-quinolone), phenazines; anti-microbial cations such as Cu, Mn, Ag, Au; or combinations thereof.

One or more of the antimicrobial agents disclosed herein may be selected to provide a polymer that is biocidal, eukaryotic non-toxic, delivers prokaryotic antimicrobial activity, or a combination thereof. In addition, the composition of the polymer, including one or more of the antimicrobial agents, may be easily modified to reduce or eliminate microbial resistance. Furthermore, the composition may be modified to provide a release fraction directed towards a specific species (e.g., "targeted antagonism").

In one embodiment, the antimicrobial agent is polymerized into or onto a polymer backbone and/or otherwise incorporated into the polymer matrix of the antimicrobial article. In another embodiment, the polymerization of the antimicrobial agent produces a cleavable linkage through hydrolysis, enzymatic action, and/or pH changes. In a further embodiment, the acid monomer, such as the diacid monomer sebacic acid, forms a hydrophilic matrix and/or provides a chemistry that facilitates surface erosion. The surface erosion properties may provide the controlled release of the antimicrobial agents and/or active moiety at the surface without affecting bulk properties of the antimicrobial article or a burst release. Additionally, the polymerization and/or incorporation of the antimicrobial agent in the antimicrobial article reduces or eliminates migration and/or blooming of the antimicrobial agent, providing uniform or substantially uniform release, chemical stability, environmental stability, uniform or substantially uniform protection on conformal surfaces, or a combination thereof.

A polymerization profile of the polymer formed according to one or more embodiments disclosed herein may provide a continuum of polymeric forms from oligomeric gels to thermoset elastomers/polymers. Additionally, the degree of polymerization of the antimicrobial article formed according to one or more embodiments disclosed herein may be varied to produce any resinous polymer form from a gel through a thermoplastic and which can further be processed into a thermoset. Furthermore, the polymer may be incorporated into a composition of matter, such as, but not limited to, an adhesive, coating, polymer blend, extrudate, additive filler, or combination thereof. For example, a PGS resin formed through water mediated synthesis, as described in one or more of the embodiments disclosed herein may, be formulated into a coating and applied to an implantable textile.

The following examples describe the invention in further detail. These examples are provided for illustrative purposes only, and should in no way be considered as limiting the invention.

Comparative Example 1

Glycerol (62.0 g, 0.670 mol) and sebacic acid (135.2 g, 0.670 mol) were added to a reactor vessel that was fitted with a chilled water condenser in a distillation setup. A nitrogen purge was applied at 5 L/min. The reactor vessel was then heated in a melt step at a mantle temperature of 140° C. in order to sufficiently melt the solid sebacic acid for 70 minutes. The temperature in the reactor was then reduced to 130° C. in a stir step and stirred at 500 RPM for 50 minutes.

After the melt and stir steps of the reaction, the reaction continued for an additional 24 hours at 120° C. and stirred at 500 RPM under nitrogen (5 L/min).

Next, a vacuum setup was connected to the distillation condenser and subatmospheric pressure was applied to the contents of the vessel. The pressure was reduced slowly and step wise (approximately 10-15% per step) over about 85 minutes to approximately 20 Torr.

Once the pressure in the reaction vessel reached approximately 20 Torr, the vacuum pump was set to 5 Torr. Following the application of vacuum, the reaction vessel was left to react for 1440 minutes at 120° C., and stirred at 500 RPM, with a sub-atmospheric pressure of approximately 5 Torr.

Upon removal of water from the reaction mixture, stir speed was reduced to 200 RPM to account for the increased viscosity of the mixture. However, the reaction was allowed to continue to react at a temperature of 120° C., with the vacuum set at 5 Torr, and stir speed of 200 RPM for an additional 1440 minutes as a PGS polymerization step.

After this period, the PGS material in the reactor vessel was transferred to a glass jar and allowed to cool on the bench top for about 45 minutes, then was transferred to a freezer for storage, where it was frozen for at least about 24 hours before testing and analysis.

Comparative Example 2

In another comparative example, a polymer was made using the method of synthesis disclosed in the '894 Patent in which equimolar amounts of glycerol and sebacic acid were reacted at 120° C. (using nitrogen instead of argon as the inert gas) for 24 hours, followed by reducing the pressure from 1 Torr to 40 mTorr over 5 hours and then maintaining the reaction at 120° C. for another 48 hours. This procedure yielded a pliable resin, not an elastomer as taught in the '894 patent.

Example 1

Glycerol (62.0 g, 0.673 mol) was added to a reactor vessel with water (37.5 g, 2.08 mol) under stirring. After dissolution of the glycerol, sebacic acid (138.0 g, 0.682 mol) was added to the reactor vessel. The reactor vessel was then fitted with a condenser to reflux water during the melt and stir steps of the PGS polymerization (condenser temperature was set to 2.5° C.). The reactor vessel was then heated to a mantle temperature of 140° C. with a stir speed of 500 RPM for approximately 70 minutes. The material in the vessel became clear once the reactor vessel reached approximately 95° C.

After the sebacic acid melted, the zone temperature was set to 130° C. and the mixture was stirred at 500 RPM under reflux for 50 minutes.

The condenser was then removed and the vessel was fitted with a distillation condenser to remove water from the vessel. A nitrogen purge was applied to the vessel (5 L/min) and the zone temperature was set to 120° C. During the distillation, the contents of the vessel were stirred at 500 RPM for 1440 minutes.

Next, a vacuum setup was connected to the distillation condenser and the subatmospheric pressure was applied to the contents of the vessel. The pressure was reduced slowly and step wise (approximately 10-15% per step) over about 85 minutes to approximately 20 Torr.

Once the pressure in the reaction vessel reached approximately 20 Torr, the vacuum pump was set to 5 Torr. Following the application of vacuum, the reaction vessel was left to react for 1440 minutes at 120° C., and stirred at 500 RPM, with the sub-atmospheric pressure set to 5 Torr.

Upon removal of water from the reaction mixture, stir speed was reduced to 200 RPM to account for the increased viscosity of the mixture. However, the reaction was allowed to continue to react at a temperature of 120° C. at pressure of approximately 5 Torr, and stir speed of 200 RPM for an additional 1440 minutes as a PGS polymerization step.

After this period, the PGS material in the reactor vessel was transferred to a glass jar and allowed to cool on the bench top for about 45 minutes, then was transferred to a freezer for storage, where it was frozen for at least about 24 hours before testing and analysis.

Example 2

To assess the impact of adding water to PGS pre-polymer following the early stages of polymerization, further reaction conditions at temperatures below 120° C. were assessed for processability of the material.

PGS pre-polymer was produced in three reactor vessels in the manner described with respect to Example 1, the pre-polymer being that material after the nitrogen purge but prior to vacuum. Following these steps, water was added to reactor vessels, and pre-polymer and water were mixed for approximately 30 min, during which a homogenous dispersion was formed. Following this step, the condensers were removed from reactor vessels and a vacuum setup was applied. The vacuum was applied to each reactor, starting at 650 Torr and, slowly, the pressure was reduced stepwise (about 10% each step) to a terminal setting of 5 Torr over the course of 100 minutes.

As vacuum reached its terminal setting, the temperature was reduced in reactor 1 to 110° C. and stirred at 500 RPM. The temperature in reactor 3 was reduced to 80° C.

Following the application of terminal vacuum, the reactions in reactors 1, 2, and 3 were allowed to continue as set forth in Table 1.

TABLE 1

| Reactor | Reactor Temp (° C.) | Stirring Rate (RPM) | Time (min) | Vacuum (Torr) |
| --- | --- | --- | --- | --- |
| 1 | 110 | 500 | 1440 | <10 |
| 2 | 120 | 500 | 1440 | <10 |
| 3 | 80 | 500 | 1440 | <10 |

Following the steps set forth in Table 1, the stir speed was lowered to 200 RPM and the reaction continued in each reactor for another 1440 minutes using the same temperature, stirring, and vacuum settings. Finally, the material from each vessel was recovered and stored in glass jars. The jars were allowed to cool to room temperature for 1 hour on the bench top, then placed in freezer for at least 24 hours prior to any analysis.

This example illustrates that water can be added to the molten pre-polymer and homogenously mixed. Then, the reaction could be continued using reaction temperatures that were lower than the standard 120° C. This allows for compounds, agents, or other reagents to be added to the reactant mixture, while polymerization continues under mild reaction conditions.

Example 3

Glycerol and sebacic acid were added in 1:1 molar amounts in water to melt the sebacic acid in a similar manner as described in Example 1 using a condenser to reflux water during the melt and stir steps, followed by distillation to remove the water once the sebacic acid was melted. The components of the vessel were stirred under nitrogen for 24 hours at 120° C. at atmospheric pressure and a nitrogen flow rate of 5 L per minute, the time measured from the point at which it was determined all water initially added had been removed by distillation. At the conclusion of that 24 hours, the pressure was reduced to 10 Torr and the temperature to 115° C., and the reaction was allowed to proceed for another 24 hours.

Example 4

A water mediated preparation of PGS was carried out by adding glycerol and sebacic acid to water in which the experiment was carried out in generally the same manner as Example 3, except that the temperature of the mixture during the 24 hour nitrogen purge step was maintained at 125° C. instead of 120° C. before the pressure reduced to 10 Torr and the temperature reduced to 115° C., upon which the reaction was allowed to proceed for another 24 hours.

Example 5

A water mediated preparation of PGS was carried out by adding glycerol and sebacic acid to water in which the experiment was carried out in generally the same manner as Example 3 with the reactants purged under nitrogen for 24 hours at 120° C. at atmospheric pressure and a nitrogen flow rate of 5 L per minute, the time measured from the point at which it was determined all water initially added had been removed by distillation, except that in this example, that was followed by 26 hours at a reduced pressure of 10 Torr and a temperature of 130° C.

The examples and comparative examples, along with various intermediates (in which some samples of pre-polymer were obtained after the nitrogen purge but before the low-pressure step) were characterized through various tests including Differential Scanning Calorimetry (DSC), Thermogravimetric Analysis (TGA), Fourier Transform Infrared (FTIR) Spectroscopy, Rheometry Analysis, a titration to determine the acid number of the PGS material, as well as gel permeation chromatography (GPC).

For DSC, the calorimeter was loaded with a sample of PGS and tested from −40° C. to 60° C. at 10° C./min, with 1 minute holds.

Focusing on the crystallization temperature ($T_C$) and first melt temperature ($T_M$) of second heat step revealed that samples only exposed to water during the melt and stir steps had results typical of Comparative Example 1 ($T_C \approx -11.4°$ C., $T_M$ about 9.5° C.) and demonstrated that by mediating the reaction with water, the reaction is slowed. Samples reacted at lower temperatures, such as in Example 2 had results ($T_C \approx -8.3°$ C., $T_M$ about 12.5° C.) that were intermediate to pre-polymer PGS ($T_C \approx -7.4°$ C., $T_M$ about 14.3° C.) and Comparative Example 1 ($T_C \approx -11.8°$ C., $T_M$ about 8.3° C.), which indicated that by reacting at lower temperatures, the reaction is slowed but continues to progress.

TGA: A sample of Example 1 was loaded into the thermogravimetric system with a program set to: (1) hold at 25° C. for 1 minute; (2) ramp to 375° C. at 25° C./min, with a nitrogen purge; (3) ramp to 475° C. at 10° C./min, with a nitrogen purge; and (4) ramp to 550° C. at 10° C./min, with an air purge. The TGA results are consistent with results obtained through analysis of Comparative Example 1 (onset at about 420° C.). The period of water mediation was determined not to affect decomposition temperature. The TGA results of Example 2 samples (onset at 415° C.) are slightly depressed compared with Comparative Example 1. These results did not show a decomposition occurring at a lower temperature (onset=about 220° C.) indicating that no reactants were present; a lower decomposition step is typically present in pre-polymer PGS samples.

Figure 3:
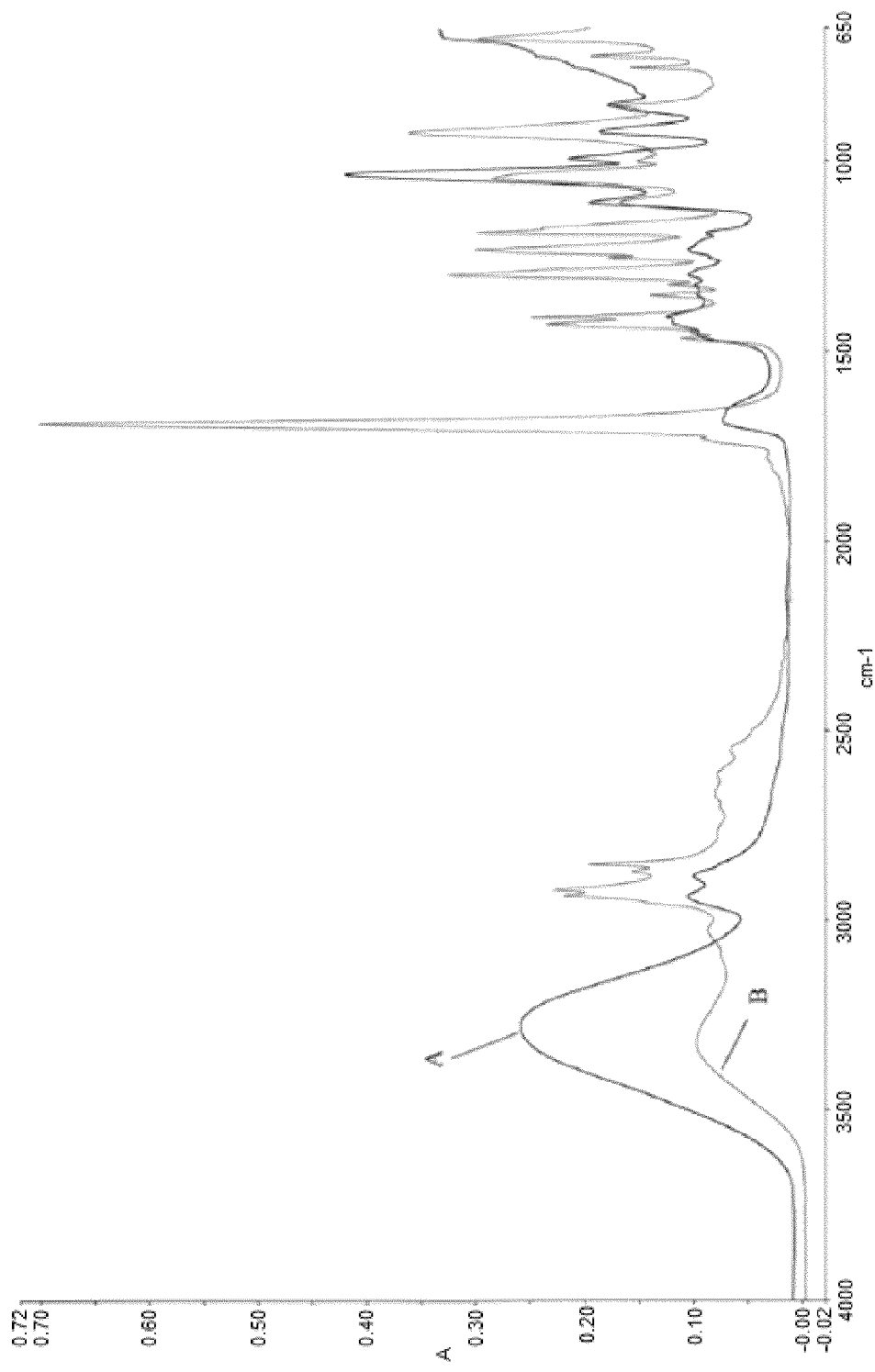
FIG. 3 graphically compares the FTIR spectra of PGS polymerization reactions after 120 minutes in (A) a water-mediated PGS polymerization reaction; and (B) a standard PGS polymerization reaction.
Figure 4:
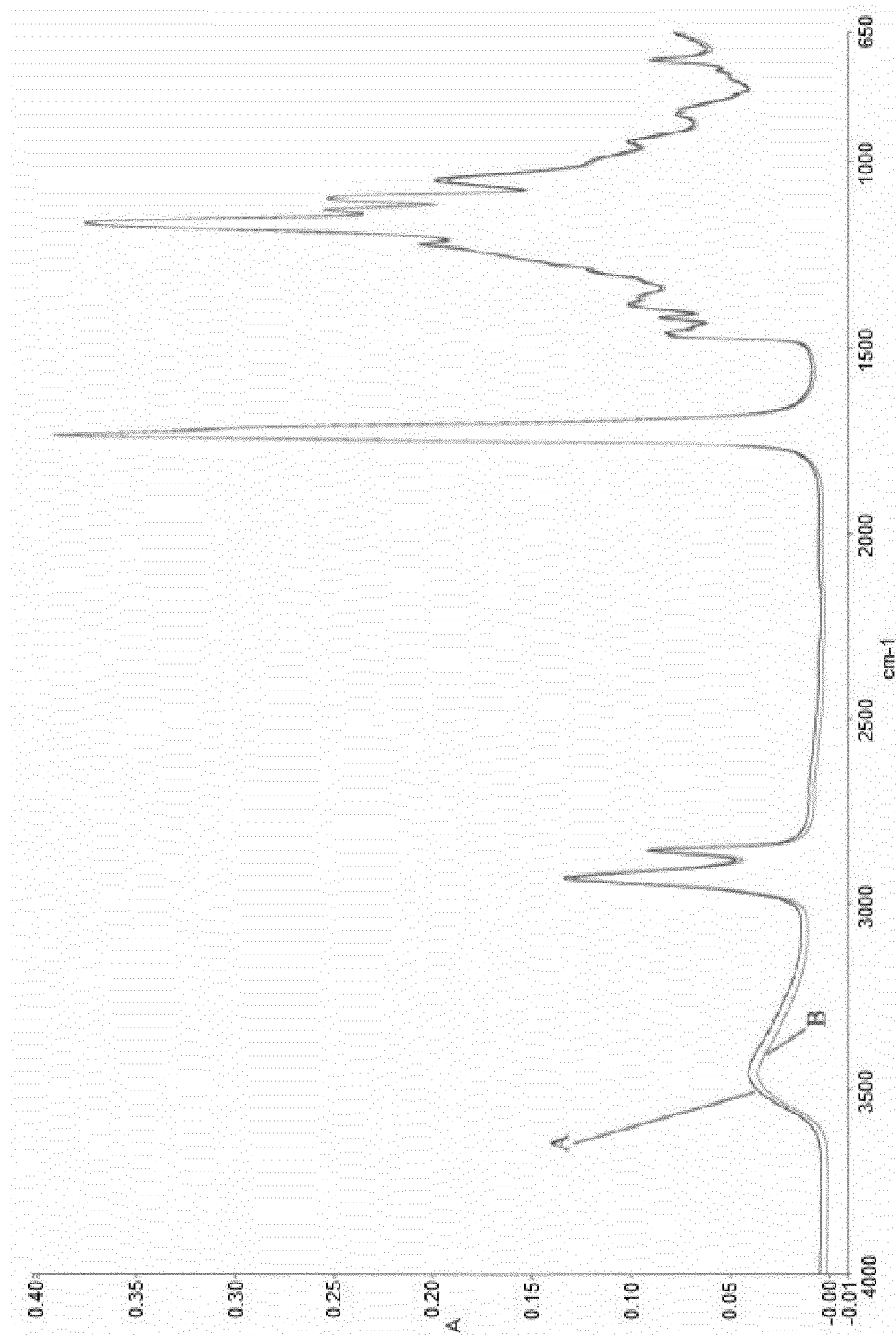
FIG. 4 graphically compares the FTIR spectra of PGS polymerization reactions after 76 hours in (A) a standard PGS polymerization reaction; and (B) a water-mediated polymerization.
Figure 5:
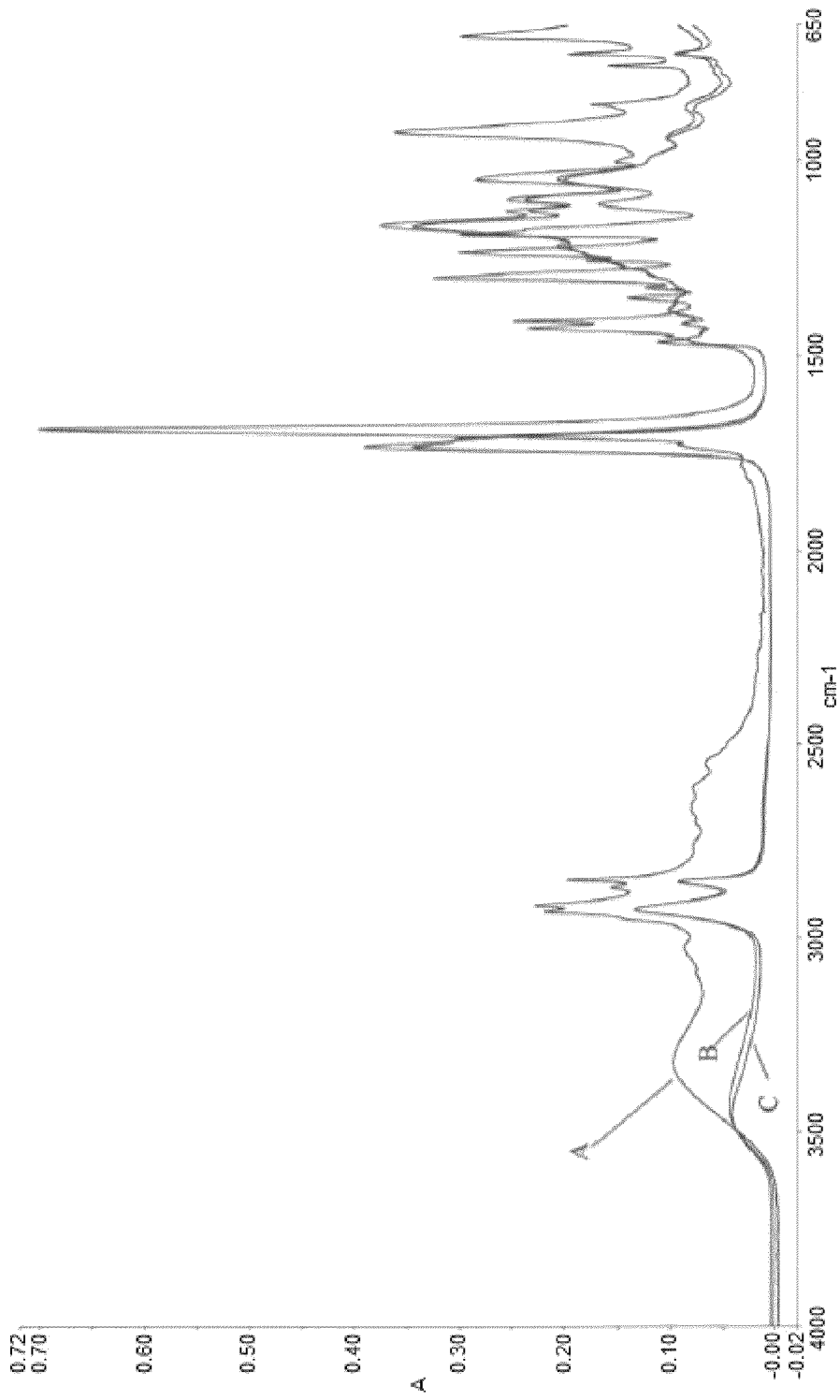
FIG. 5 graphically compares the FTIR spectra of PGS polymerization reactions in (A) a standard PGS polymerization reaction at 120 minutes; (B) a low temperature, water-mediated PGS polymerization reaction; and (C) a standard PGS polymerization reaction at 76 hours.

FTIR: A sample of Example 1 was analyzed by FTIR-ATR with 32 scans at a 4 cm-1 resolution, across the range of 4000-650 cm-1. FIG. 3 shows FTIR spectra of Comparative Example 1 (dashed) and Example 1 (solid) reactant mixtures at 120 min following reaction commencement. FIG. 4 shows FTIR spectra of Comparative Example 1 (dashed) and Example 1 (solid) reactant mixtures at the conclusion of the PGS reaction (i.e., at the end of the full 48 hour reaction process). FIG. 5 shows FTIR spectra of Example 2 (solid) with Comparative Example 1 after 120 min (dark dashed) and 76 hours (light dashed) following reaction commencement.

Spectra show ingrowth of ester carbonyl peak at 1735 cm$^{-1}$ compared to pre-polymer (120 min) and Comparative Example 1 material.

Rheology: An amplitude sweep and frequency sweep study was performed on Example 1 samples that were molded into a thin layer on aluminum pans, then stored in the freezer for about 24 hours prior to testing. The flattened samples were placed on the rheometer in flat slabs, while the gap was set to minimize FN on the sample while loading it onto the rheometer. All samples (amplitude sweep and frequency sweep) were allowed to relax in the rheometer hood at 25° C. for at least 10 minutes before analysis.

The molten sample rotational flow curve at 80° C. show results that illustrate small changes in PGS material when the reaction is mediated with water. Samples that are mediated only during the melt and stir steps show viscosities that are at or slightly lower than Comparative Example 1 (3.8 Pa-s (water-mediated) vs. 4.0 Pa-s (standard non-water mediated).

Similar tests were carried out on Example 2 material with the rotational flow curve at 80° C. revealing a viscosity intermediate to pre-polymer PGS and Comparative Example 1. (<1.0 Pa-s (pre-polymer PGS); 1.2 Pa-s (Example 2); 4.0 Pa-s (Comparative Example 1)).

Acid Number Analysis: Samples of the PGS were weighted into 50 mL beakers. Approximately 10 mL of isopropyl alcohol (IPA) was added to each beaker. The beakers were then covered with paraffin film, then sonicated for 10 minutes. Then, 4 drops of p-naphthol benzein solution were added to each beaker, including a 10 mL IPA blank. All samples were then titrated to a uniform green color using an IPA/KOH titrant.

Figure 6:
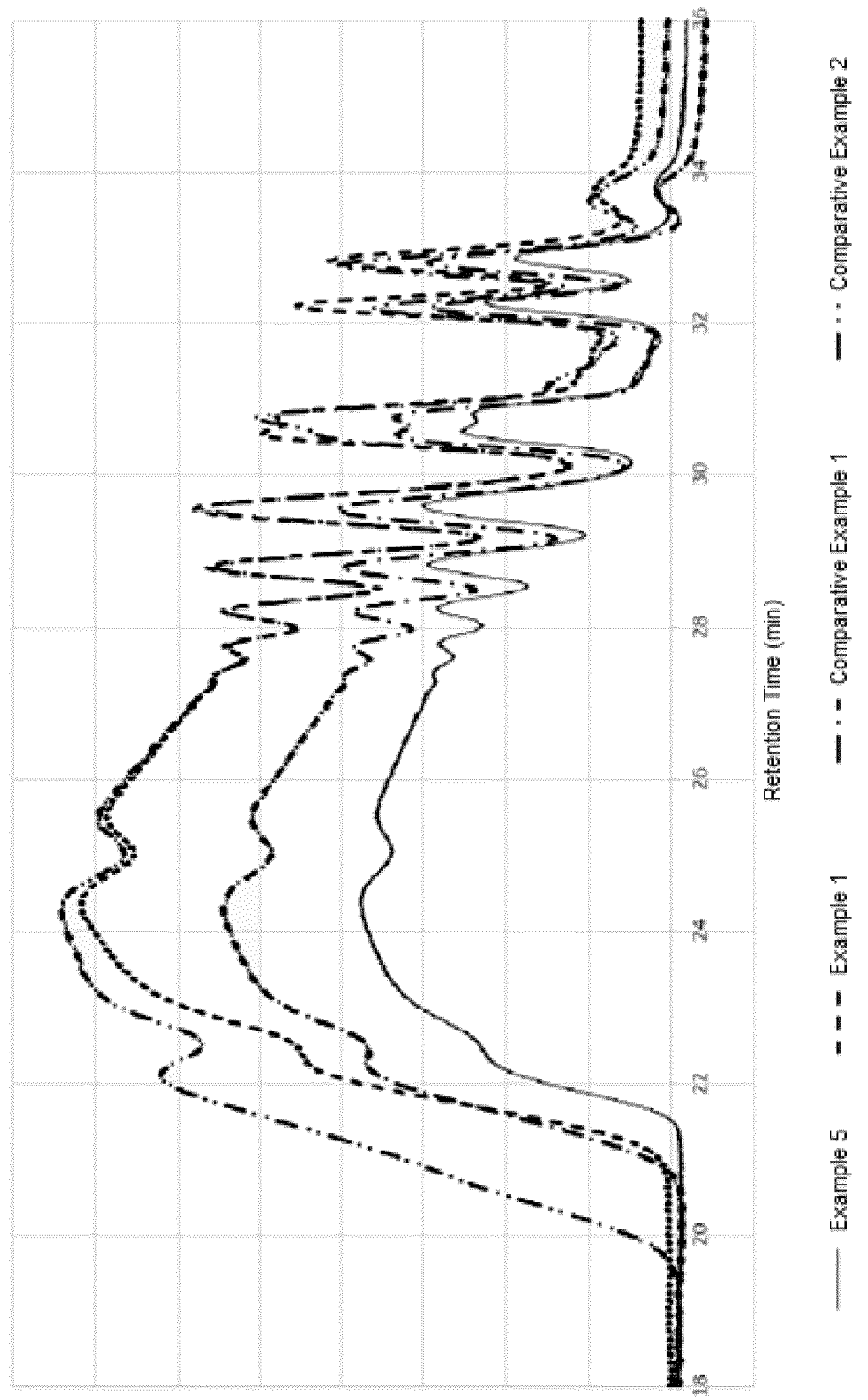
FIG. 6 graphically illustrates GPC chromatograms of PGS polymerization of water mediated polymerization reactions and a comparative non-water mediated polymerization reaction.

GPC analysis was conducted to evaluate molecular weight and to calculate polydispersity index. FIG. 6 graphically illustrates the results of Examples 1 and 5 along with Comparative Examples 1 and 2.

Molecular weight (Weight Average), polydispersity index (weight average molecular weight divided by number average molecular weight), and acid number are summarized below in Table 2.

TABLE 2

| | Molecular Weight | Polydispersity Index | Acid Number (mg/g) |
|---|---|---|---|
| Example 1 | 14663 | 7.3 | 42.8 |
| Example 5 | 12474 | 6.4 | 42.7 |
| Comparative Example 1 | 16771 | 8.2 | 43.0 |
| Comparative Example 2 | 29306 | 13.1 | 37.8 |

Among the conclusions that can be drawn from the GPC results are that water mediation results in achieving a lower molecular weight polymer and a lower polydispersity index that enable easier processing of the polymeric resin prior to any cross-linking.

Example 6

A low molecular weight (oligomeric) PLA (having a molecular weight determined by GPC of ~893 g/mol) was created by melt condensation reaction of L-(+)-lactic acid at 150° C. with stirring. The reaction was conducted for 120 min under a 5 L/min N$_2$ purge, followed by 120 min at 97 torr, then 240 min at 30 torr.

A low molecular weight (oligomeric) PGS (having a weight average molecular weight determined by GPC of ~5336 g/mol) was formed by melt polycondensation reaction of equimolar amounts glycerol and sebacic acid at 120° C. with stirring at 24 hrs under a 5 L/min N$_2$ purge followed by 24 hrs of stirring at 10 torr.

The two oligomeric components were mixed (90:10 PGS:PLA molar ratio) in a reaction vessel at 120° C. and 10 torr with stirring for about 19 hours. The resulting polymer, a viscous liquid, was then tested against neat PGS resin. Molecular weights (weight average) as determined by GPC were about 28,986 for the copolymer and about 12,453 for the PGS.

The copolymer was observed to be more elastic, less stiff and less sticky and had better recovery than the neat PGS. Differential scanning calorimetry (DSC) demonstrated the Tc of the experimental copolymers was about –23° C. compared to about –12° C. for the neat PGS, while rotational melt flow rheology and amplitude sweep rheology both demonstrated that the copolymer exhibited more liquid-like characteristics than the neat PGS.

Samples of the oligomeric PGS/PLA copolymer and the neat PGS polymer where also thermoset by further processing at 120° C. and 10 torr for 72 hours. The resulting thermosets were tested for peak load, strain at break, and modulus, the results of which are shown below in Table 3.

TABLE 3

| | neat PGS | oligomeric PGS/PLA copolymer |
|---|---|---|
| Peak Load (N) | 3.0 | 2.5 |
| Strain at Break (%) | 19 | 27 |
| Modulus (MPa) | 3.9 | 1.4 |

Example 7

The PLA of Example 6 was used and mixed with a PGS prepolymer (having a weight average molecular weight determined by GPC of ~2252 g/mol) that was formed by melt polycondensation reaction of equimolar amounts glycerol and sebacic acid at 120° C. with stirring at 24 hrs under a 5 L/min N$_2$ purge. The two components were mixed (90:10 PGS:PLA molar ratio) in a reaction vessel at 120° C. and 10 torr with stirring for about 24 hours. The resulting polymer was a low viscosity liquid that was then thermoset at 120° C. and 10 torr for 72 hours and compared against neat PGS as shown in Table 4. Molecular weight (weight average) as determined by GPC was about 10,853 for the copolymer.

TABLE 4

| | neat PGS | PGS prepolymer/PLA copolymer |
|---|---|---|
| Peak Load (N) | 3.0 | 1.5 |
| Strain at Break (%) | 19 | 26 |
| Modulus (MPa) | 3.9 | 0.83 |

Examples 8 and 9

Examples 8 and 9 were made in the same manner as Examples 6 and 7, respectively, but were instead combined at 5:5 molar ratios; molecular weights (weight average) as determined by GPC were about 129,720 for Example 8 and 16,340 for Example 9.

DSC analysis showed that Examples 6 and 7 demonstrated a semi-crystalline structure while Examples 8 and 9 were amorphous in nature.

Examples 10-12

Water mediated preparations of low and high molecular weight PGS (Examples 10 and 11, respectively) were prepared in accordance with the embodiments described herein and subjected to antimicrobial testing following the method described in JIS Z2801:2000 Antimicrobial properties—Test for antimicrobial activity and efficacy; AMD No. 1—May 20, 2006. In addition, a PGS resin made in accordance with the water mediated preparations described herein was further processed into a thermoset (Example 12) and was also tested under the same methodology. All three samples exhibited antimicrobial activity values of >99% against both *Escherichia coli* and *Staphylococcus aureus*.

A number of patent and non-patent publications may be cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and consisting of."

What is claimed is:

1. A method of preparing a polymeric material, comprising the steps of:
    combining an alcohol monomer and an aqueous liquid in a vessel;
    adding an acid monomer to the vessel;
    removing water from the vessel; and
    producing the polymeric material from the vessel, wherein the polymeric material comprises a polyester of the alcohol monomer and the acid monomer.

2. The method of claim 1, comprising the step of refluxing the alcohol monomer, the aqueous liquid, and the acid monomer in the vessel.

3. The method of claim 1, wherein the alcohol monomer comprises glycerol.

4. The method of any one of the preceding claims, wherein the aqueous liquid comprises a water-soluble agent.

5. The method of claim 4, wherein the water-soluble agent comprises a vitamin, an anti-inflammatory agent, a protein, a protease, an herbicide, an aquarium food source, a growth factor, a glycoprotein, a proteoglycan, an anti-mitotic agent, an antiplatelet agent, an anti-coagulant agent, an anti-thrombotic agent, a thrombolytic agent, an enzyme, a chemotherapeutic agent, an antibiotic agent, an immunological adjuvant, a scaffolding material, a processing agent, or a combination thereof.

6. The method of claim 1, wherein the aqueous liquid is water.

7. The method of claim 1, wherein the acid monomer comprises a diacid.

8. The method of claim 7, wherein the diacid comprises a compound of the formula [$HOOC(CH_2)_nCOOH$], wherein n=1-30.

9. The method of claim 8, wherein the diacid comprises malonic acid, succinic acid, glutaric acid, adipic acid, pimelic acid, suberic acid, azelaic acid, sebacic acid, or a combination thereof.

10. The method of claim 8, wherein the diacid is sebacic acid.

11. The method of claim 1, wherein the step of combining the alcohol monomer and the aqueous liquid comprises heating the alcohol monomer and the aqueous solution to about 50-200° C.

12. The method of claim 1, wherein the step of combining the alcohol monomer and the aqueous liquid comprises heating the alcohol monomer and the aqueous solution to about 90-110° C.

13. The method of claim 1, wherein the step of combining the alcohol monomer and the aqueous liquid comprises heating the alcohol monomer and the aqueous solution for a period of about 5 minutes to about 240 minutes.

14. The method of claim 1, wherein the step of removing the water comprises heating the vessel to about 50-200° C.

15. The method of claim 1, comprising reacting the acid monomer and alcohol monomer at atmospheric pressure under an inert atmosphere for about 1 hour to about 48 hours.

16. The method of claim 15, further comprising applying a sub-atmospheric pressure for about 1 hour to about 76 hours after the step of reacting at atmospheric pressure under an inert atmosphere.

17. The method of claim 1, comprising producing the polymeric material by applying a sub-atmospheric pressure for about 1 hour to about 76 hours.

18. The method of claim 1 further comprising adding a co-monomer or a polymer to the vessel to form the polymeric material as a co-polymer.

19. The method of claim 18, wherein the co-monomer comprises a diacid, lactic acid, caprolactone, or a combination thereof.

20. The method of claim 1 further comprising reacting the produced polymeric material to form a co-polymer.

21. The method of claim 20, wherein the polymeric material is poly(glycerol sebacate) and the co-polymer is formed by reacting the poly(glycerol sebacate) with poly(lactic acid).

22. A method of preparing a polymeric material, comprising the steps of:
  combining glycerol and water in a vessel;
  adding sebacic acid to the vessel;
  removing water from the vessel;
  reacting the glycerol and sebacic acid in the vessel at atmospheric pressure and a temperature in the range of 50-200° C. in the presence of an inert gas for a period of about 1 hour to about 48 hours;
  applying a sub-atmospheric pressure to the vessel for about 1 hour to about 76 hours after the step of reacting in the presence of an inert gas at atmospheric pressure, with a temperature in the vessel in the range of 50-200° C. thereby forming a polymeric material in the vessel.

23. The method of claim 22, wherein the sub-atmospheric pressure is in the range of 5 Torr to 20 Torr.

24. The method of claim 22, wherein the sub-atmospheric pressure is applied for about 24 hours to about 36 hours.

25. An article of manufacture prepared by the method of claim 1.

26. A bioabsorbable polymeric material prepared by the process of claim 1, comprising poly(glycerol sebacate).

27. The bioabsorbable polymeric material of claim 26, wherein the bioabsorbable polymeric material has anti-microbial characteristics.

* * * * *